(12) United States Patent
Strobl

(10) Patent No.: US 8,454,560 B2
(45) Date of Patent: Jun. 4, 2013

(54) SYRINGE MOUNT FOR A MEDICAL FLUID INJECTOR

(75) Inventor: Geoffrey S. Strobl, Williamsburg, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 1317 days.

(21) Appl. No.: 11/567,011

(22) Filed: Dec. 5, 2006

(65) Prior Publication Data

US 2008/0132839 A1 Jun. 5, 2008

(51) Int. Cl.
*A61M 37/00* (2006.01)
*A61M 5/32* (2006.01)
*A61B 19/00* (2006.01)

(52) U.S. Cl.
USPC .......................................... 604/131; 604/414

(58) Field of Classification Search
USPC ................. 604/151–154, 181, 187, 140, 500, 604/403–416, 130–131
See application file for complete search history.

(56) References Cited

U.S. PATENT DOCUMENTS

| | | |
|---|---|---|
| 3,964,139 A | 6/1976 | Kleinmann et al. |
| 3,983,363 A | 9/1976 | Alter |
| 4,217,993 A | 8/1980 | Jess et al. |
| 4,265,618 A | 5/1981 | Herskovitz et al. |
| 4,422,942 A | 12/1983 | Allington |
| 4,460,355 A | 7/1984 | Layman |
| 4,560,979 A | 12/1985 | Rosskopf |
| 4,628,499 A | 12/1986 | Hammett |
| 4,634,431 A | 1/1987 | Whitney et al. |
| 4,650,465 A | 3/1987 | Langer et al. |
| 4,743,228 A | 5/1988 | Butterfield |
| 4,755,172 A | 7/1988 | Baldwin |
| 4,812,724 A | 3/1989 | Langer et al. |
| 4,854,324 A | 8/1989 | Hirschman et al. |
| 4,913,703 A | 4/1990 | Pasqualucci et al. |
| 4,931,041 A | 6/1990 | Faeser |
| 4,950,246 A | 8/1990 | Muller |
| 4,994,984 A | 2/1991 | Massimo |
| 5,069,225 A | 12/1991 | Okamura |
| 5,078,698 A | 1/1992 | Stiehl et al. |
| 5,135,511 A | 8/1992 | Houghton et al. |
| 5,178,609 A | 1/1993 | Ishikawa |
| 5,242,408 A | 9/1993 | Jhuboo et al. |
| D341,760 S | 11/1993 | Armbruster et al. |
| 5,261,884 A | 11/1993 | Stern et al. |
| 5,269,762 A | 12/1993 | Armbruster et al. |

(Continued)

FOREIGN PATENT DOCUMENTS

| | | |
|---|---|---|
| EP | 1486219 A1 | 12/2004 |
| WO | 01/37903 A2 | 5/2001 |
| WO | 02/056947 A1 | 7/2002 |

*Primary Examiner* — Philip R Wiest

(57) ABSTRACT

In certain embodiments, a syringe mount of the invention may include a plate, an actuator, and one or more movable members located between the plate and the actuator. Each of the plate and the actuator may have an orifice defined therein, and an imaginary reference axis of the syringe mount may extend through one or both of these orifices. The actuator may be movable relative to the plate in a direction substantially perpendicular to the reference axis. Further, the moveable member(s) may be designed to move (e.g., pivot) toward the reference axis due to movement of the actuator from a first position to a second position and to move (e.g., pivot) away from the reference axis due to movement of the actuator from the second position to the first position.

38 Claims, 13 Drawing Sheets

U.S. PATENT DOCUMENTS

| | | | |
|---|---|---|---|
| 5,295,966 A | 3/1994 | Stern et al. |
| 5,300,031 A | 4/1994 | Neer et al. |
| 5,322,511 A | 6/1994 | Armbruster et al. |
| 5,383,858 A | 1/1995 | Reilly et al. |
| 5,425,716 A | 6/1995 | Kawasaki et al. |
| D360,462 S | 7/1995 | Armbruster et al. |
| 5,505,704 A | 4/1996 | Pawelka et al. |
| 5,509,901 A | 4/1996 | Milijasevic |
| 5,512,730 A | 4/1996 | Spinello |
| 5,520,653 A | 5/1996 | Reilly et al. |
| D370,974 S | 6/1996 | Barresi et al. |
| 5,611,784 A | 3/1997 | Barresi et al. |
| 5,662,612 A | 9/1997 | Niehoff |
| 5,672,155 A | 9/1997 | Riley et al. |
| 5,741,232 A | 4/1998 | Reilly et al. |
| 5,779,675 A | 7/1998 | Reilly et al. |
| 5,795,333 A | 8/1998 | Reilly et al. |
| RE35,979 E | 12/1998 | Reilly et al. |
| 5,873,861 A | 2/1999 | Hitchins et al. |
| 5,899,885 A | 5/1999 | Reilly et al. |
| 5,928,197 A | 7/1999 | Niehoff |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,964,736 A | 10/1999 | Lane |
| 5,968,015 A | 10/1999 | Yamamoto |
| 5,997,502 A | 12/1999 | Reilly et al. |
| 6,017,326 A | 1/2000 | Pasqualucci et al. |
| 6,042,565 A | 3/2000 | Hirschman et al. |
| D422,356 S | 4/2000 | Marano et al. |
| 6,048,334 A | 4/2000 | Hirschman et al. |
| 6,059,754 A | 5/2000 | Pasch et al. |
| 6,080,136 A | 6/2000 | Trull et al. |
| 6,090,064 A | 7/2000 | Reilly et al. |
| 6,090,071 A | 7/2000 | Kriesel |
| 6,091,058 A | 7/2000 | Faries, Jr. et al. |
| 6,099,502 A | 8/2000 | Duchon et al. |
| 6,159,183 A | 12/2000 | Neer et al. |
| 6,200,289 B1 | 3/2001 | Hochman et al. |
| 6,221,045 B1 | 4/2001 | Duchon et al. |
| 6,241,708 B1 | 6/2001 | Reilly et al. |
| 6,245,041 B1 | 6/2001 | Kriesel |
| 6,245,043 B1 | 6/2001 | Villette |
| 6,254,572 B1 | 7/2001 | Knipfer et al. |
| 6,259,067 B1 | 7/2001 | Faries, Jr. et al. |
| 6,269,340 B1 | 7/2001 | Ford et al. |
| 6,312,410 B1 | 11/2001 | Yamamoto |
| 6,322,535 B1 | 11/2001 | Hitchins et al. |
| RE37,487 E | 12/2001 | Reilly et al. |
| 6,336,913 B1 | 1/2002 | Spohn et al. |
| 6,344,030 B1 | 2/2002 | Duchon et al. |
| 6,368,307 B1 | 4/2002 | Ziemba et al. |
| 6,371,938 B1 | 4/2002 | Reilly et al. |
| 6,402,717 B1 | 6/2002 | Reilly et al. |
| 6,454,743 B1 | 9/2002 | Weber |
| 6,475,192 B1 | 11/2002 | Reilly et al. |
| 6,582,408 B1 | 6/2003 | Bach-Rasmussen et al. |
| 6,607,508 B2 | 8/2003 | Knauer |
| 6,610,033 B1 | 8/2003 | Melanson et al. |
| 6,652,489 B2 | 11/2003 | Trocki |
| 6,656,157 B1 | 12/2003 | Duchon et al. |
| 6,673,033 B1 | 1/2004 | Sciulli et al. |
| 6,673,048 B1 | 1/2004 | Duchon |
| 6,676,634 B1 | 1/2004 | Spohn et al. |
| 6,676,635 B2 | 1/2004 | Nemoto |
| 6,716,195 B2 | 4/2004 | Nolan, Jr. et al. |
| 6,726,657 B1 | 4/2004 | Dedig et al. |
| 6,733,478 B2 | 5/2004 | Reilly et al. |
| 6,743,205 B2 | 6/2004 | Nolan, Jr. et al. |
| 6,808,513 B2 | 10/2004 | Reilly et al. |
| 6,821,013 B2 | 11/2004 | Reilly et al. |
| 6,854,620 B2 | 2/2005 | Ramey |
| 6,921,384 B2 | 7/2005 | Reilly et al. |
| 6,958,053 B1 | 10/2005 | Reilly |
| 6,974,443 B2 | 12/2005 | Reilly et al. |
| 6,997,904 B2 | 2/2006 | Sculati |
| 7,025,757 B2 | 4/2006 | Reilly et al. |
| 7,029,459 B2 | 4/2006 | Reilly |
| 7,081,105 B2 | 7/2006 | Reilly et al. |
| 7,101,352 B2 | 9/2006 | Duchon et al. |
| 7,273,477 B2 * | 9/2007 | Spohn et al. ............... 604/500 |
| 2002/0107481 A1 | 8/2002 | Reilly et al. |
| 2003/0028145 A1 | 2/2003 | Duchon et al. |
| 2003/0233069 A1 | 12/2003 | Gillespie, Jr. et al. |
| 2004/0015124 A1 | 1/2004 | Sciulli et al. |
| 2004/0068223 A1 | 4/2004 | Reilly |
| 2004/0092878 A1 | 5/2004 | Flaherty |
| 2004/0116861 A1 | 6/2004 | Trocki et al. |
| 2004/0133153 A1 | 7/2004 | Trocki et al. |
| 2004/0133161 A1 | 7/2004 | Trocki et al. |
| 2004/0133162 A1 | 7/2004 | Trocki et al. |
| 2004/0133183 A1 | 7/2004 | Trocki et al. |
| 2004/0249276 A1 * | 12/2004 | Nemoto et al. ............ 600/432 |
| 2006/0106347 A1 | 5/2006 | Fago et al. |

* cited by examiner

SYRINGE MOUNT FOR A MEDICAL FLUID INJECTOR

FIELD OF INVENTION

The present invention generally relates to injectors for injecting fluid into animal subjects, including humans, and particularly relates to syringe mounts used to operatively connect a syringe to an injector.

BACKGROUND

During many medical procedures, various fluids are injected into patients for purposes of diagnosis or treatment. An example of one such fluid is contrast media used to enhance angiography, magnetic resonance imaging, or computerized tomography imaging. Such fluids may also be used in other modalities, such as intravenous pyelogram (IVP) and cardiology. The injectors used in these procedures are often automated devices that expel fluid from a syringe, through a tube, and into a patient.

Injectors suitable for these applications generally utilize relatively large volume syringes and tend to be capable of producing relatively large flow rates and injection pressures. For these reasons, injectors for such applications typically include large, high mass injection motors and drive trains. The motor and drive train of an injector are typically housed in an injection head, which is supported by a floor, wall, or a ceiling mounted arm. In order to perform an injection procedure using one of these injectors, a syringe may be operatively connected to an injector (e.g., via a face plate thereof), and a drive ram of the injector may then be moved to expel fluid from the syringe. Thereafter, the drive ram may be retracted, and the used syringe may then be disconnected from the injector.

SUMMARY

The present invention relates to a syringe mount that may be utilized to assist in enabling a user to mount a syringe on a medical fluid injector (e.g., in preparation for a medical imaging procedure) and to enable a user to subsequently remove the syringe from the injector (e.g., upon completion of an medical imaging procedure). Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of features and aspects that may not be set forth below.

A first aspect of the invention is directed to a syringe mount for connecting a syringe to a medical fluid injector. This syringe mount includes a movable actuator that has a wall member, which includes a distally facing wall surface, a proximally facing wall surface, and an orifice defined in the actuator. In addition, the syringe mount also includes a first movable member that is operatively coupled to the actuator and that confronts the distally facing wall surface of the actuator. As used herein, components that are "operatively coupled" may be directly coupled to one another or indirectly coupled to one another, may be integral with one another, or may be separate components.

A second aspect of the invention is also directed to a syringe mount for connecting a syringe to a medical fluid injector. The syringe mount of this second aspect includes a structure (e.g., a plate, a housing, or other structure of the syringe mount), an actuator, and at least one movable member located between the structure and the actuator. Each of the structure and the actuator has an orifice defined therein, and an imaginary reference axis of the syringe mount extends through both of these orifices. The actuator is movable relative to the structure in a direction substantially perpendicular to the reference axis. Further, the moveable member(s) is(are) designed to move (e.g., pivot) toward the reference axis due to movement of the actuator from a first position to a second position and to move (e.g., pivot) away from the reference axis due to movement of the actuator from the second position to the first position.

Yet a third aspect of the invention is directed to a method of using a syringe mount of a medical fluid injector (e.g., to mount a syringe on an injector for an injection procedure). In this method, a syringe is inserted into an orifice defined in a first component (e.g., an actuator) of the syringe mount. The first component of the syringe mount is moved in a direction substantially perpendicular to a longitudinal axis of the syringe while the syringe is located within the orifice. Due to this movement of the first component, a second component (e.g., a movable member) of the syringe mount is moved toward the longitudinal axis of the syringe.

Still a fourth aspect of the invention is directed to a method of using a syringe mount of a medical fluid injector (e.g., to remove a syringe from an injector upon completion of an injection procedure). In this method, a first component (e.g., an actuator) of the syringe mount is moved in a direction substantially perpendicular to a longitudinal axis of a syringe while the syringe is located within an orifice defined in the first component of the syringe mount. A second component (e.g., a movable member) of the syringe mount is moved away from the syringe, and the syringe is removed from the syringe mount after the first and second components of the syringe mount have been moved.

Various refinements exist of the features noted above in relation to the various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DETAILED DESCRIPTION OF EXEMPLARY EMBODIMENTS

Figure 1:
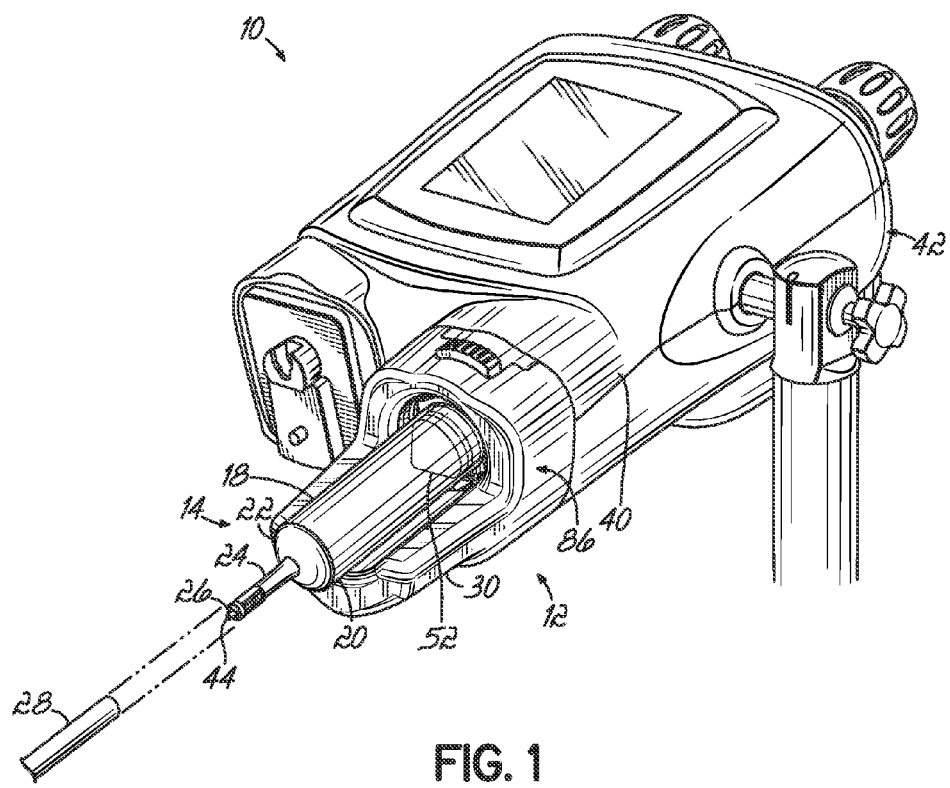
FIG. 1 is a perspective view of an injector head of an injector, having a syringe attached to a forward area thereof.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time-consuming, but would nevertheless be a routine undertaking of design, fabrication, and manufacture for those of ordinary skill having the benefit of this disclosure.

Referring to the Figures, an injector 10 includes a syringe mount 12 to facilitate attachment of a syringe 14 to the injector 10 in alignment with a drive ram 16, in order to provide an injection assembly. The syringe 14 for use with the injector 10 generally includes a body 18 (which may be in the form of an exterior cylindrical barrel), which at its forward end 20, is integral with a conical front wall 22. A neck 24, terminating in a discharge tip 26, generally extends forwardly from and may be integral with the conical front wall 22. The body 18 of the syringe 14 may interface with an interior wall of a pressure jacket (not shown) or a cradle 30 when such a pressure jacket or cradle 30 is present on the injector 10. The syringe 14, as used in conjunction with the injector 10 of the present invention, includes a syringe mating section 32, which may be in the form of a radially outwardly extending flange 34. This flange 34 is positioned in a plane substantially perpendicular to a longitudinal axis 36 of the syringe 14 and may generally be integral with the rearward end 38 of the body 18 of the syringe 14. When the syringe 14 is associated with the injector 10, the flange 34 is positioned into and/or in contact with the syringe mount 12 located on the forward end 40 of a housing 42 of the injector 10. The syringe mating section 32 and syringe mount 12 may be utilized to facilitate operative connection of the syringe 14 to the injector 10, as will be described in greater detail below.

The discharge tip 26 of the syringe 14 has an orifice 44 defined in its remote end, which may communicate with an internal syringe cavity 46 defined within the neck 24, the conical front wall 22, and the body 18 of the syringe 14. A rearward end 48 of the cavity 46 may be defined by a generally forward facing surface 50 of a syringe plunger 52. In the illustrated embodiment, this forward facing surface 50 is substantially conical. The surface 50 may be of a slope that conforms to the slope of the interior of the conical front wall 22. The syringe plunger 52 may be snugly slidable within the body 18 of the syringe 14 such that the cavity 46 is of variable volume. Tubing (not shown) may be operatively connected to the discharge tip 26 such that fluid can be expressed from the syringe 14 through the tubing.

Figure 4B:
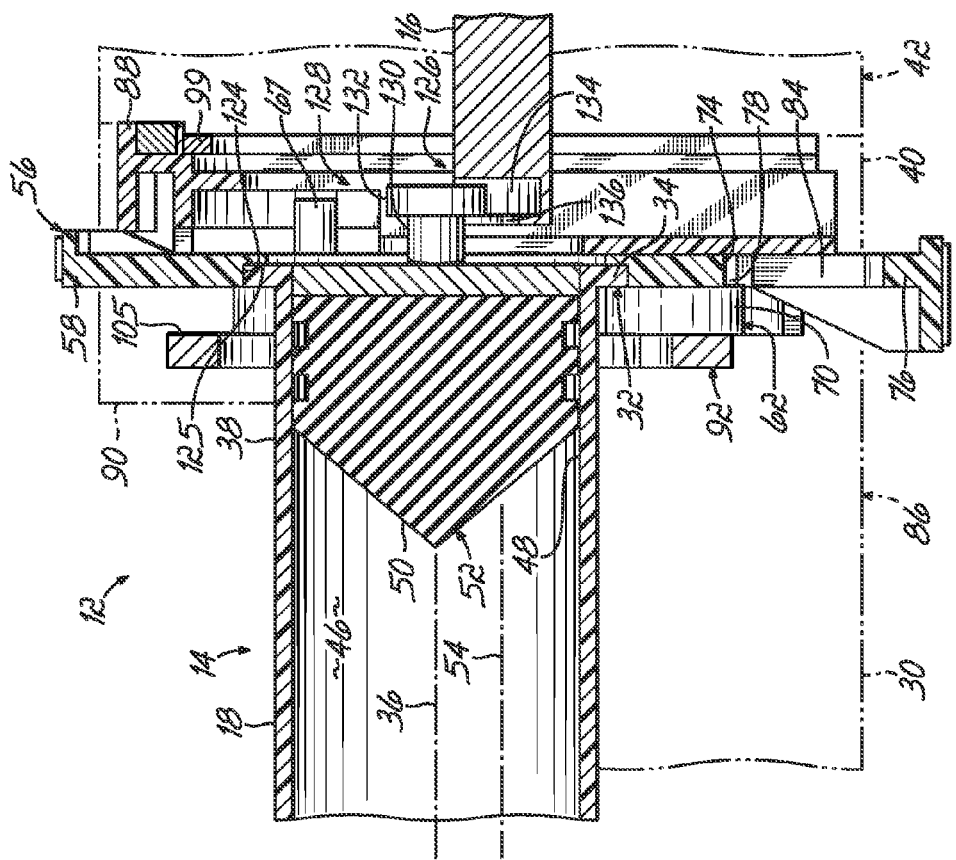
FIG. 4B is a cross-sectional view, taken along line 4B-4B of FIG. 4A, and also shows a coupling mechanism of a syringe plunger positioned in proximity to a plunger coupling element of a drive ram.
Figure 5B:
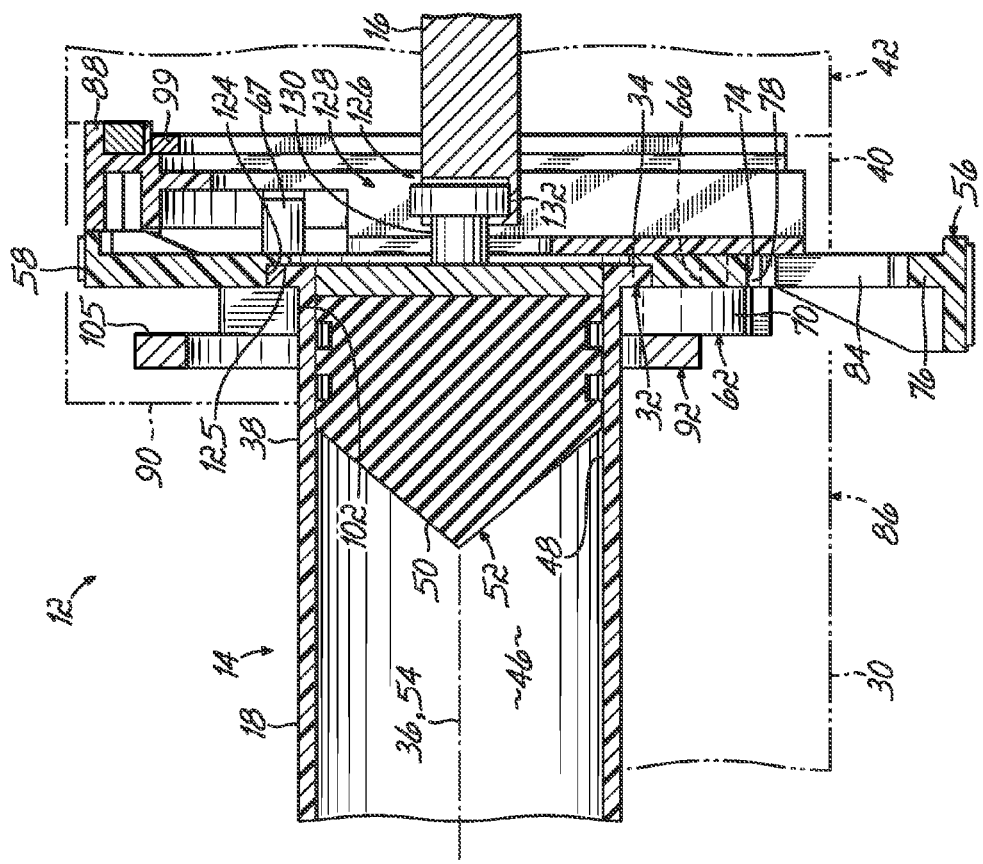
FIG. 5B is a cross-sectional view, taken along line 5B-5B of FIG. 5A, and also shows the coupling mechanism on the backside of the syringe plunger engaged with the plunger coupling element of the drive ram.
Figure 5A:
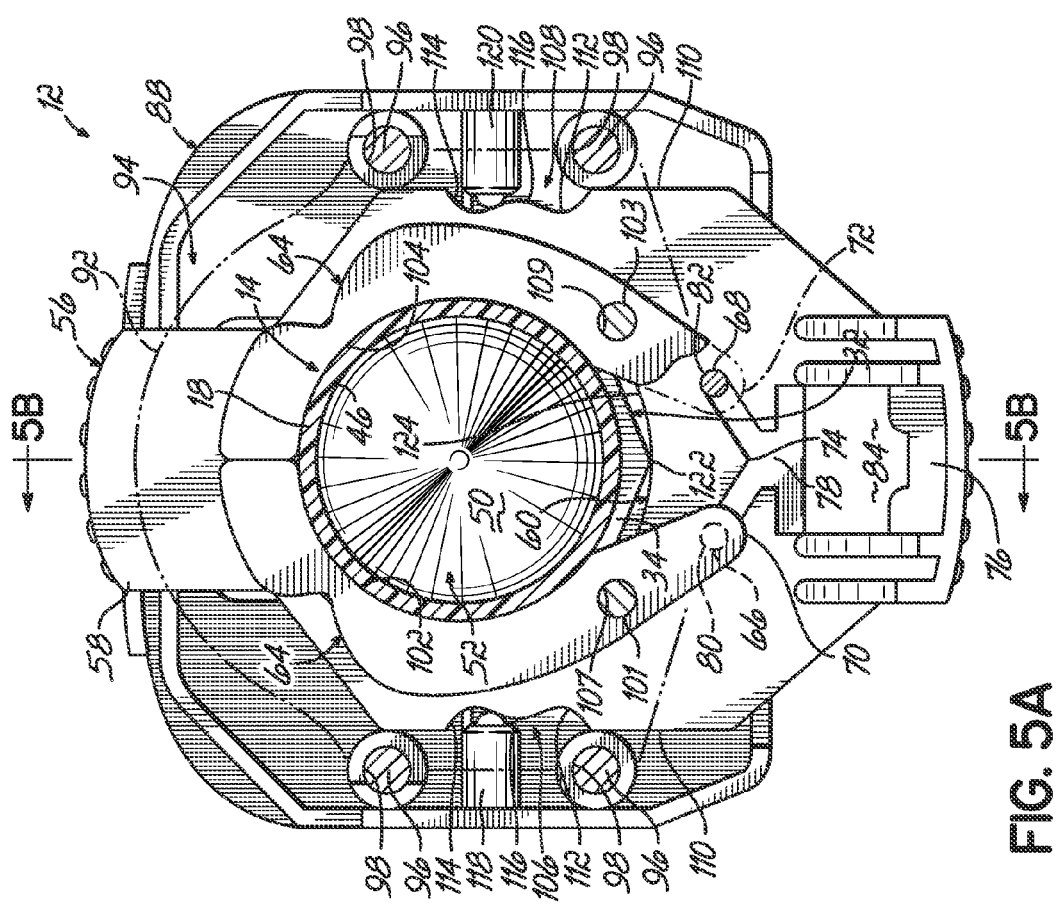
FIG. 5A is a cutaway view of the syringe mount of FIG. 2B, particularly showing the first and second movable members in a closed position and engaging a syringe.
Figure 6:
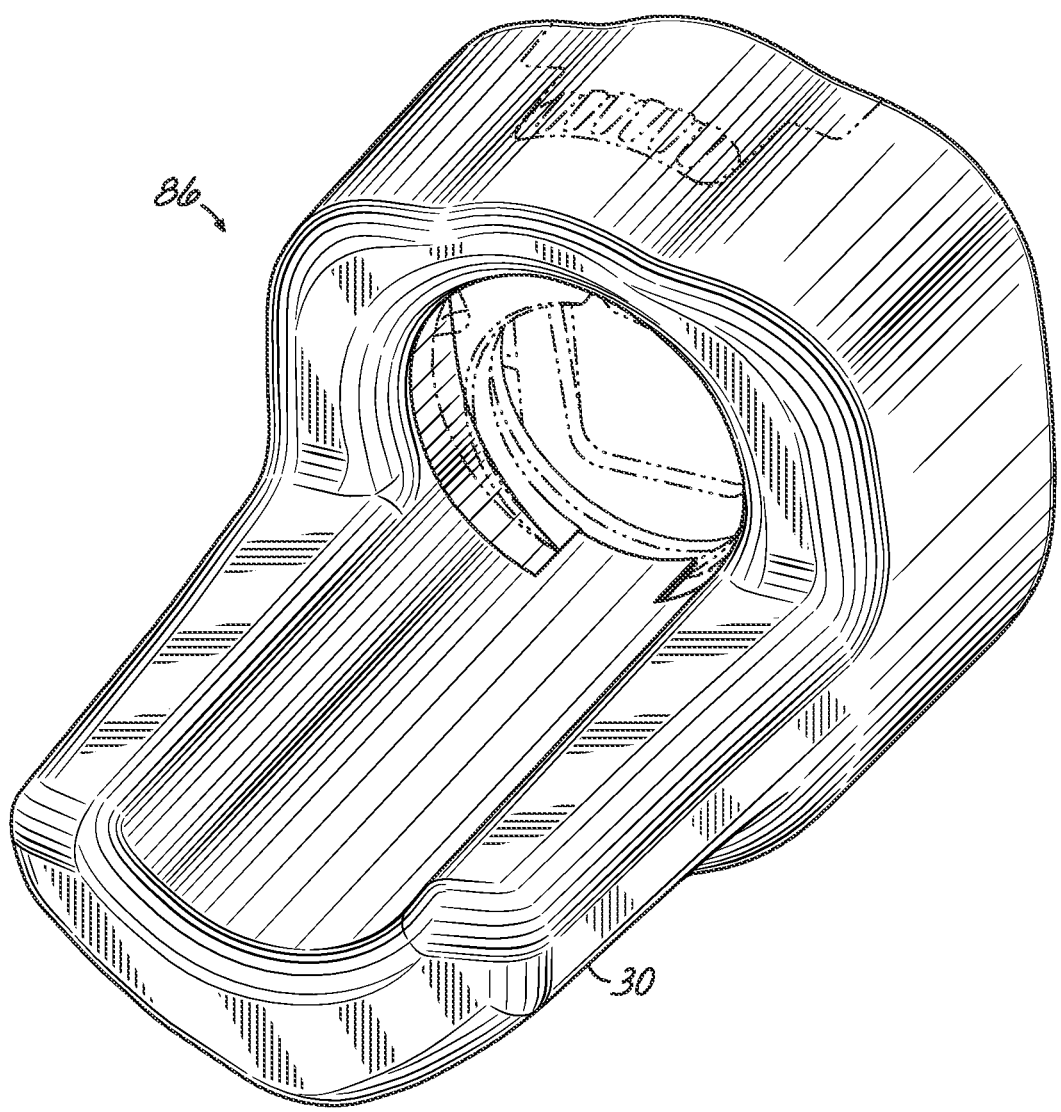
FIG. 6 is a perspective view of a face plate of an injector in accordance with the principles of the present invention.
Figure 7:
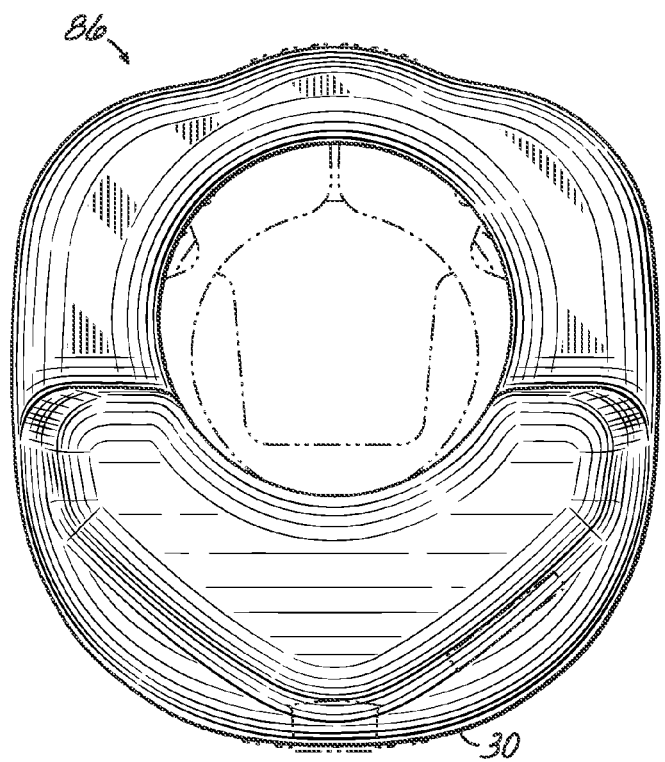
FIG. 7 is a front view of the face plate of FIG. 6.
Figure 8:
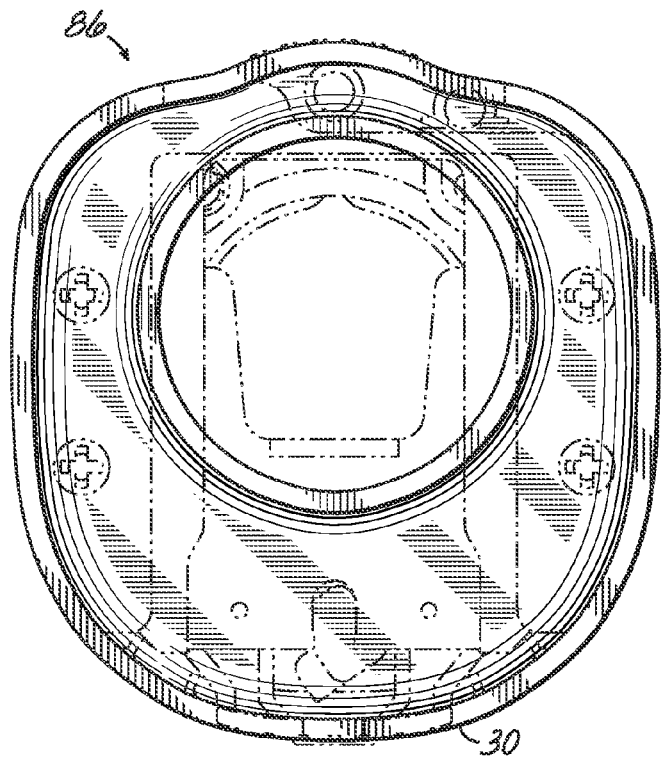
FIG. 8 is a rear view of the face plate of FIG. 6.
Figure 9:
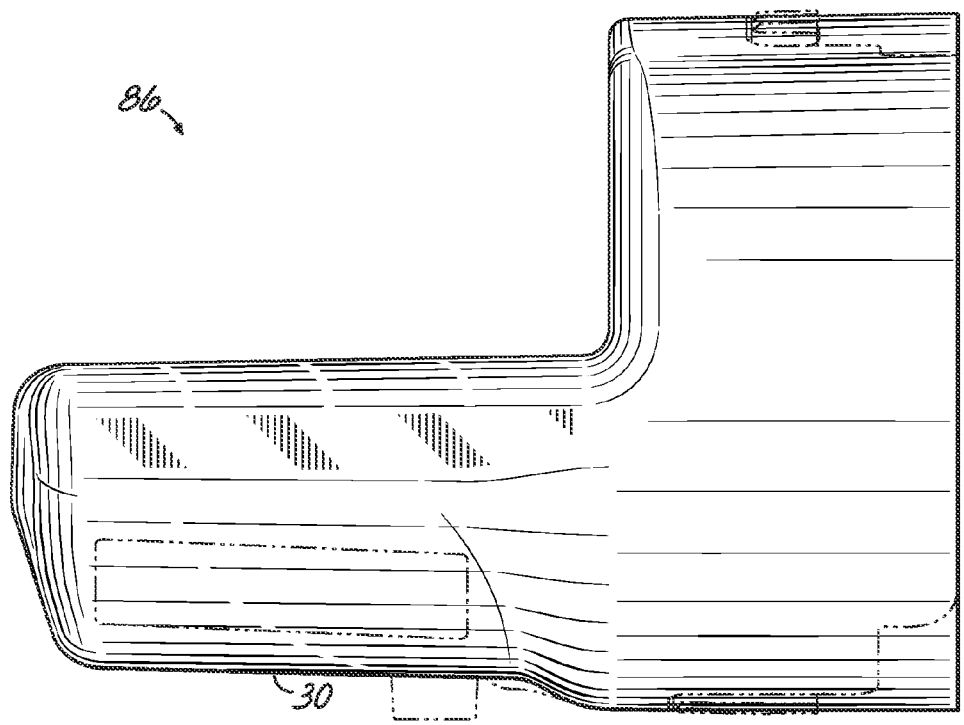
FIG. 9 is a side view of the face plate of FIG. 6.
Figure 10:
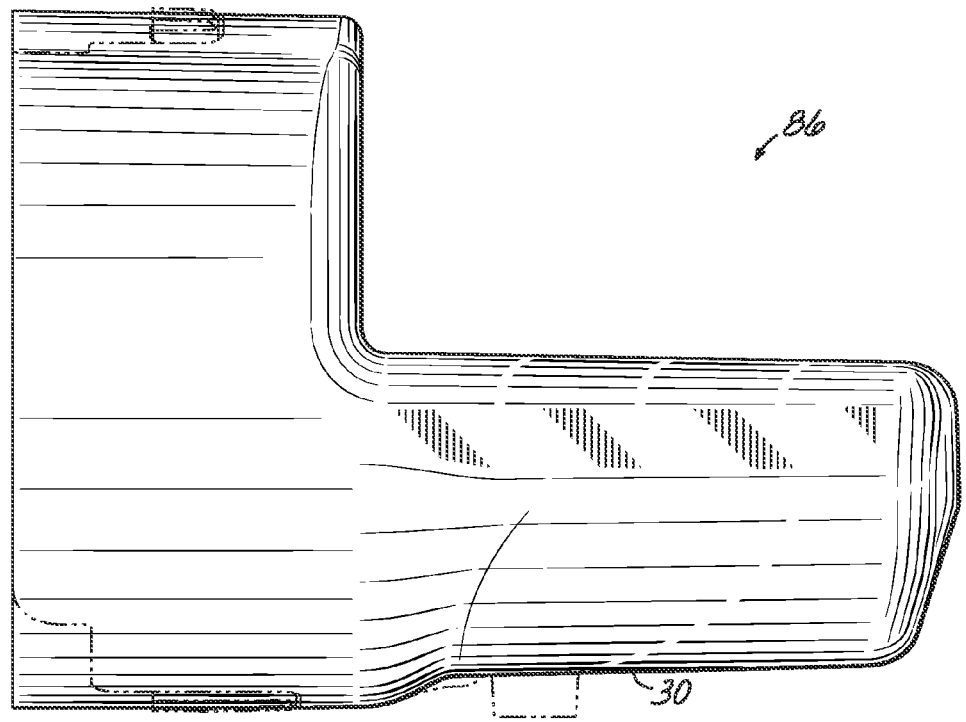
FIG. 10 is a side view of the face plate of FIG. 6 taken from the opposite side from that shown in FIG. 9.
Figure 12:
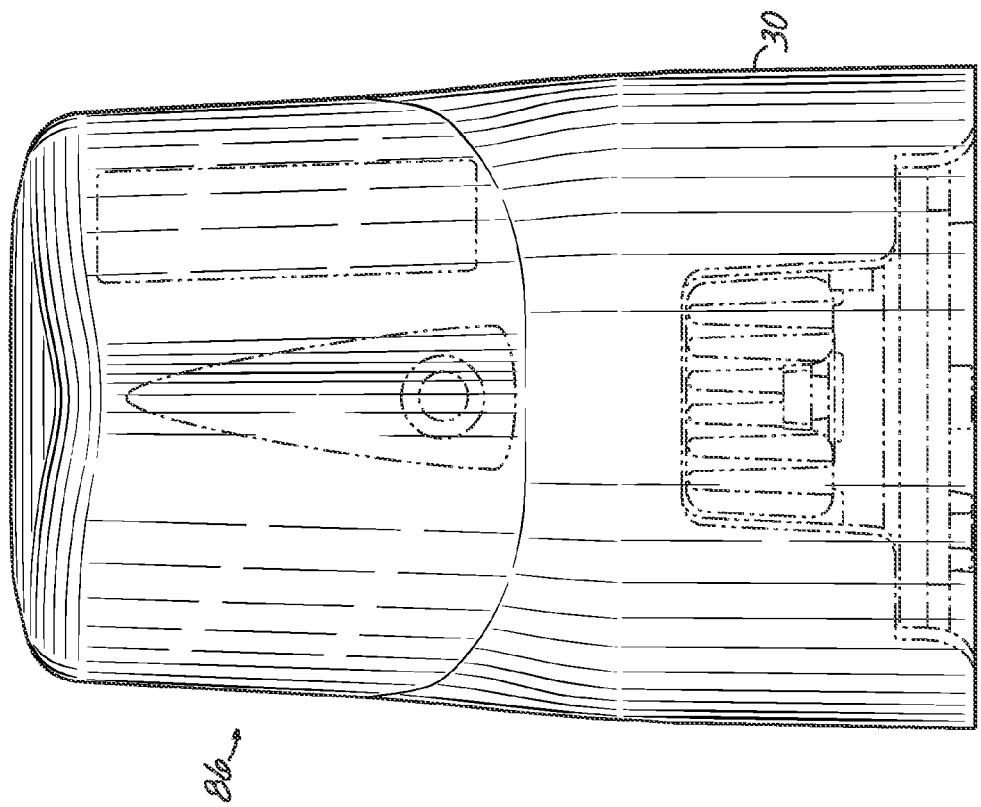
FIG. 12 is a bottom view of the face plate of FIG. 6.
Figure 11:
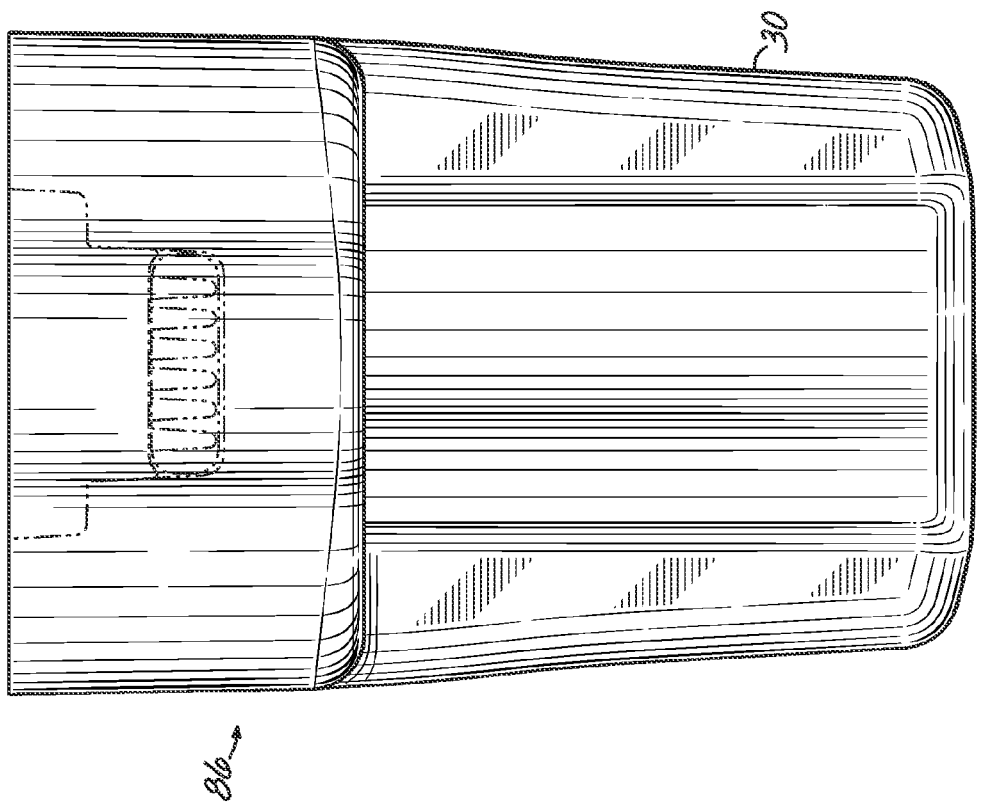
FIG. 11 is a top view of the face plate of FIG. 6.
Figure 13:
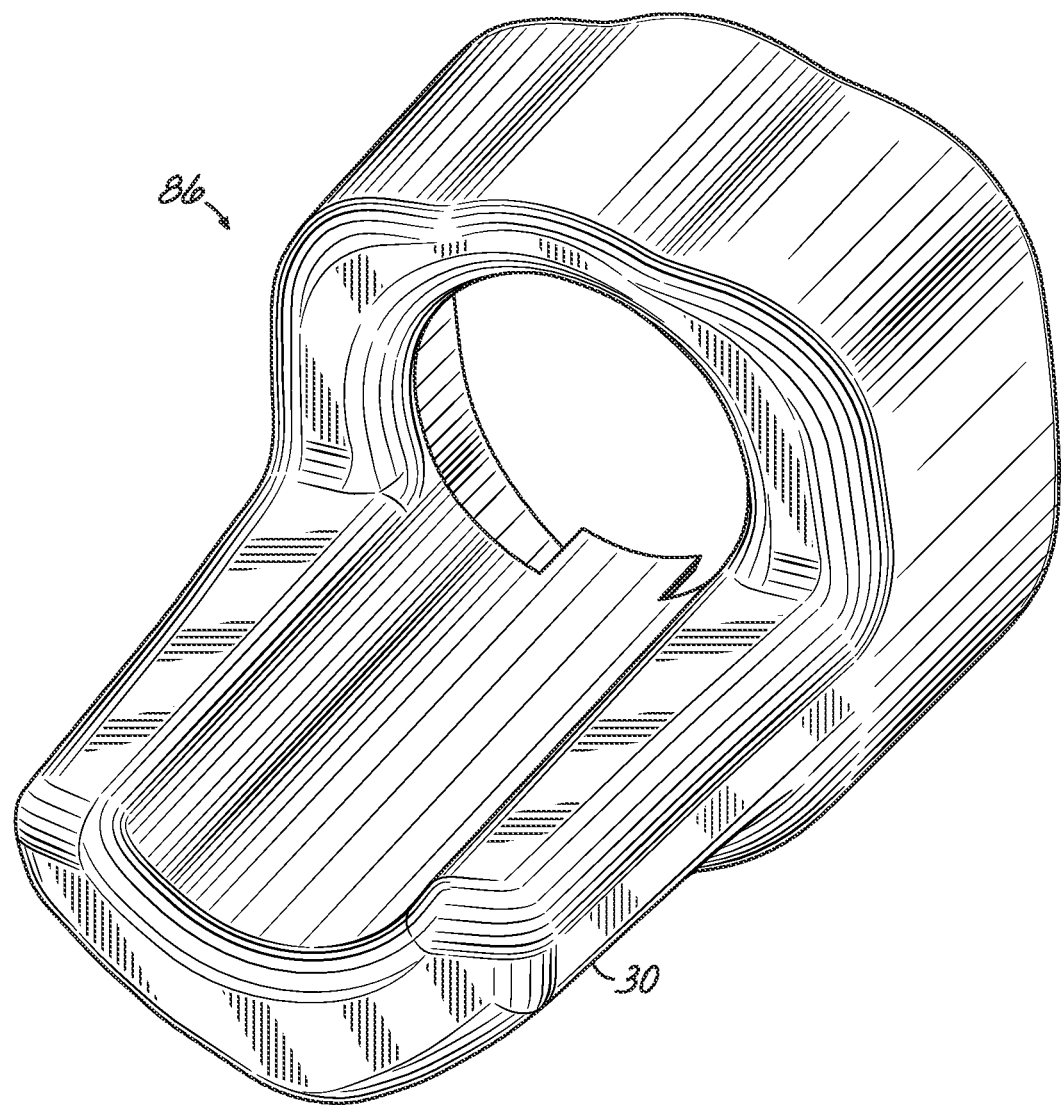
FIG. 13 is a perspective view of a face plate of an injector in accordance with the principles of the present invention.
Figure 14:
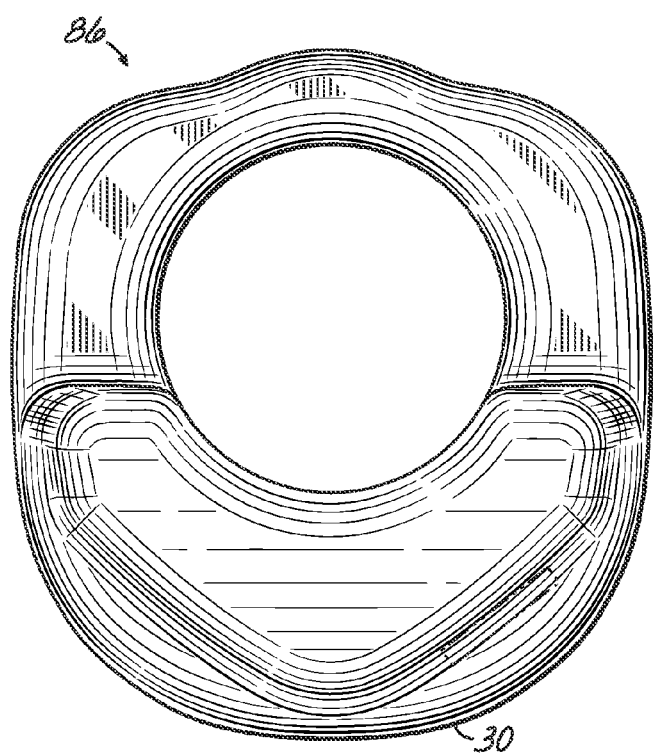
FIG. 14 is a front view of the face plate of FIG. 13.
Figure 15:
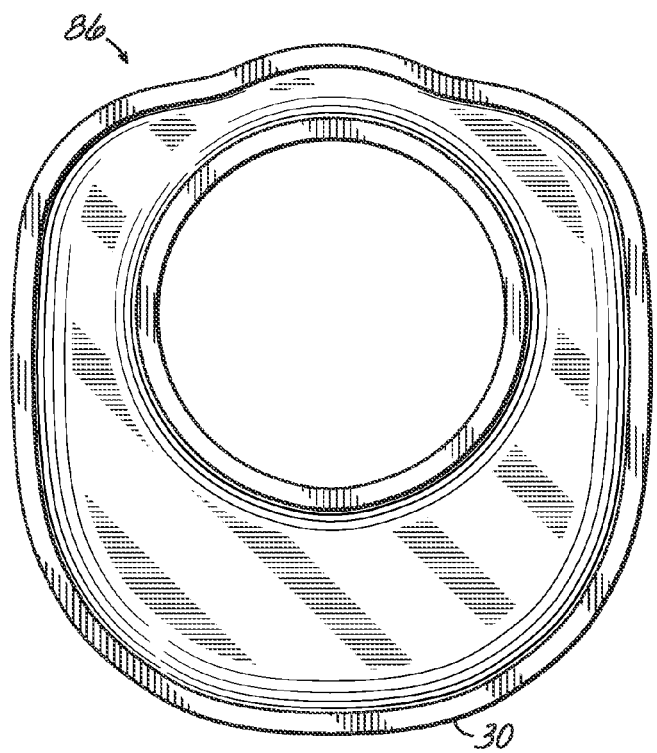
FIG. 15 is a rear view of the face plate of FIG. 13.
Figure 16:
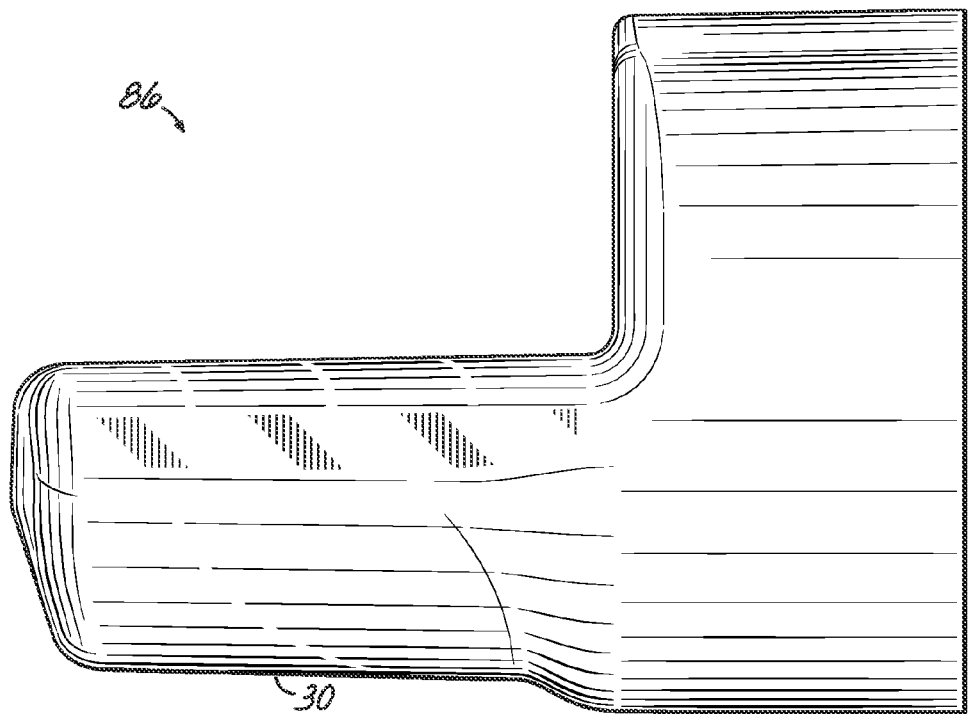
FIG. 16 is a side view of the face plate of FIG. 13.
Figure 17:
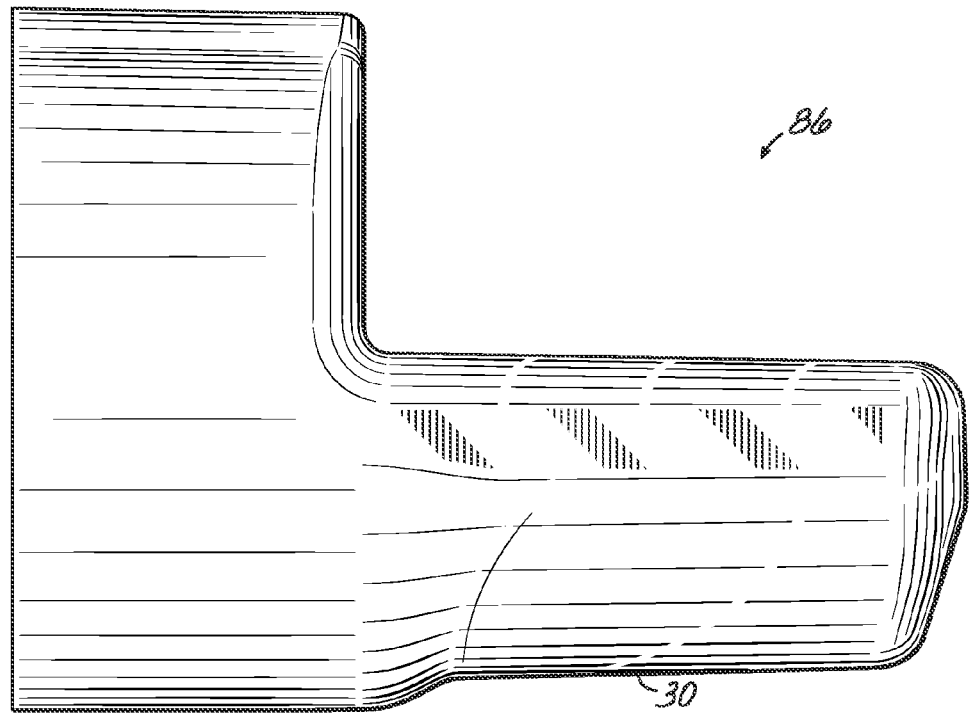
FIG. 17 is a side view of the face plate of FIG. 13 taken from the opposite side from that shown in FIG. 9.
Figure 19:
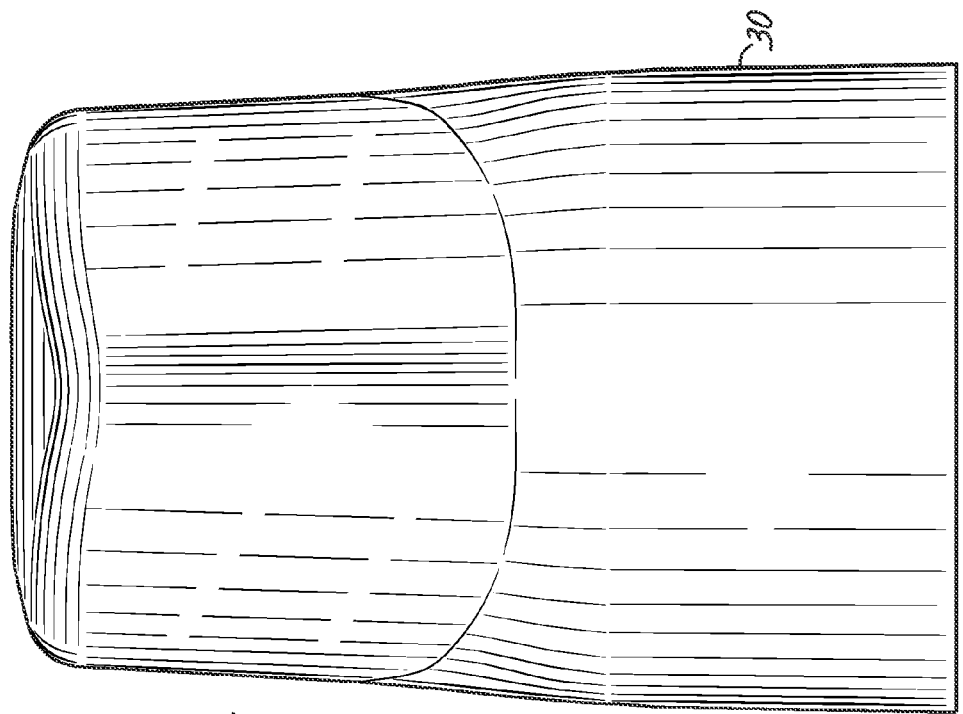
FIG. 19 is a bottom view of the face plate of FIG. 13.
Figure 18:
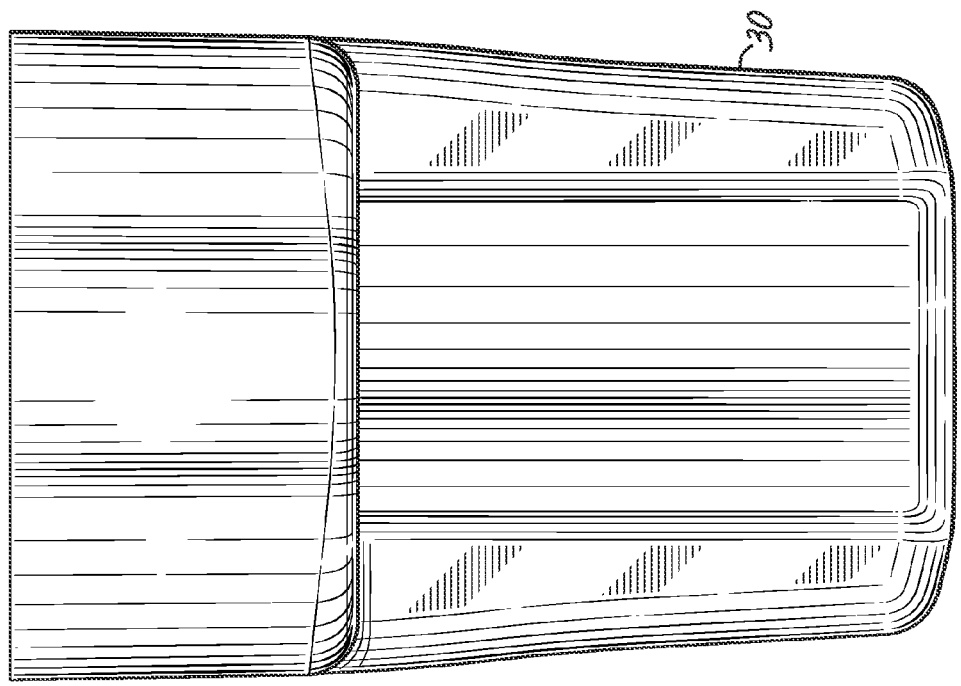
FIG. 18 is a top view of the face plate of FIG. 13.

Referring now to FIGS. 1, 4B, and 5B, the syringe plunger 52 can be seen more clearly within the body 18 of the syringe 14. When the syringe 14 is attached to the injector 10, the syringe plunger 52 is preferably located proximal to and in substantial alignment with the drive ram 16 of the injector 10. The drive ram 16 is driven by a motor (not shown) to move in a forward or rearward motion along its longitudinal axis 54 to deploy the drive ram 16, and thus to responsively deploy the syringe plunger 52 in a forward or rearward motion along the longitudinal axis 36 of the syringe 14, to inject fluid into a patient or to fill the syringe 14 with fluid, respectively. For example, one may load a prefilled syringe into the injector 10 and, by deploying the plunger 52 in a forward direction, may thereby expel fluid from the syringe 14. In so doing, the fluid may be injected into the patient. Alternatively, an empty syringe may be loaded into the injector 10 while the syringe plunger 52 may be located at or near its forward-most position. Thereafter, fluid (e.g., contrast media) may be loaded into the syringe 14 by operatively connecting the syringe 14 to a source of fluid and retracting the syringe plunger 52 in a rearward direction in order to draw fluid into the syringe 14.

The injector 10 may be designed to accommodate prefilled syringes or empty syringes of varying volumes. For example, the injector 10 may be adapted to receive 125 ml prefilled syringes (e.g., Ultraject® syringe commercially available from Mallinckrodt Inc. of St. Louis, Mo.). Such syringes may be used for injecting contrast media into a patient. These 125 ml syringes may be prefilled with any of a range of appropriate amounts of fluid, such as 50 ml, 75 ml, 100 ml, 125 ml, or other amount. Additionally, the injector 10 may accommodate an empty syringe of any of a variety of sizes (e.g., 50 ml, 75 ml, 100 ml, 125 ml, 130 ml, etc.).

Referring now to FIGS. 2A-5B, one embodiment of a syringe mount 12 is shown. The syringe mount 12 includes a movable actuator 56 including a wall member 58 defining an orifice 60, and at least a first movable member 62 operatively coupled to the actuator 56 and responsively movable therewith. More specifically, the syringe mount 12 of the illustrated embodiment includes first and second movable members 62, 64 that are operatively coupled to the wall member 58 of the actuator 56. The first and second movable members 62, 64 include first and second pins 66, 68 operatively connected thereto. The first pin 66 is operatively coupled near a first end 70 of the first movable member 62, and the second pin 68 is operatively coupled near a first end 72 of the second movable member 64. The first and second pins 66, 68 are received in at least one slot 74 defined in the wall member 58 of the actuator 56, to couple the first and second movable members 62, 64 thereto. The actuator 56 is disposed proximally of the first and second movable members 62, 64. Further, the first and second members 62, 64 may include first and second rods 67, 69 projecting rearwardly therefrom. These first and second rods 67, 69 may confront and move along the outer contour of the wall member 58 of the actuator 56, as the first and second movable members 62, 64 move between open and closed positions.

The slot 74 is defined by the wall member 58 of the actuator 56 at a base portion 76 thereof. The first and second pins 66, 68 are movable (e.g., slidable and optionally rotatable) within the slot 74. Each of the first and second pins 66, 68 can move from a position proximal to the center 78 of the slot 74, to positions near first and second terminal ends 80, 82 of the slot 74. The first and second pins 66, 68 do not both move on one side of the slot 74. Rather, the first pin 66 is adapted to move within one portion of the slot 74, and the second pin 68 is adapted to move within another portion of the slot 74. In particular, in the illustrated embodiment, a base portion 76 of the wall member 58 includes an opening 84 having a top portion thereof in a shape at least generally similar to a "V." The first and second pins 66, 68 are disposed in the "V" portion of this opening 84. When the first and second pins 66, 68 are positioned near the intersection of the two legs of the "V," the first and second movable members 62, 64 are in an open position (see FIG. 4A). When the first and second pins 66, 68 are positioned near the first and second terminal ends 80, 82 of the "V," the first and second movable members 62, 64 are in a closed position (see FIG. 5A). While the slot 74 of the illustrated embodiment is shown and described here as generally having a "V" shape, it will be recognized by those skilled in the art that such a "V" shape is not necessary, and any other shape can be used that allows the first and second movable members 62, 64 to move sufficiently within a slot to operatively connect a syringe to an injector 10. For example, the slot 74 may have a "U" or "C" shape. Further, those skilled in the art will recognize that more than one slot may be used. For example, two slots forming a "V" shape proximal to the base 76 of the wall member 58 can receive the first and second pins 66, 68 near the point of the "V." Again, those skilled in the art will recognize that the slots do not necessarily have to be in the shape of a "V."

Figure 2B:
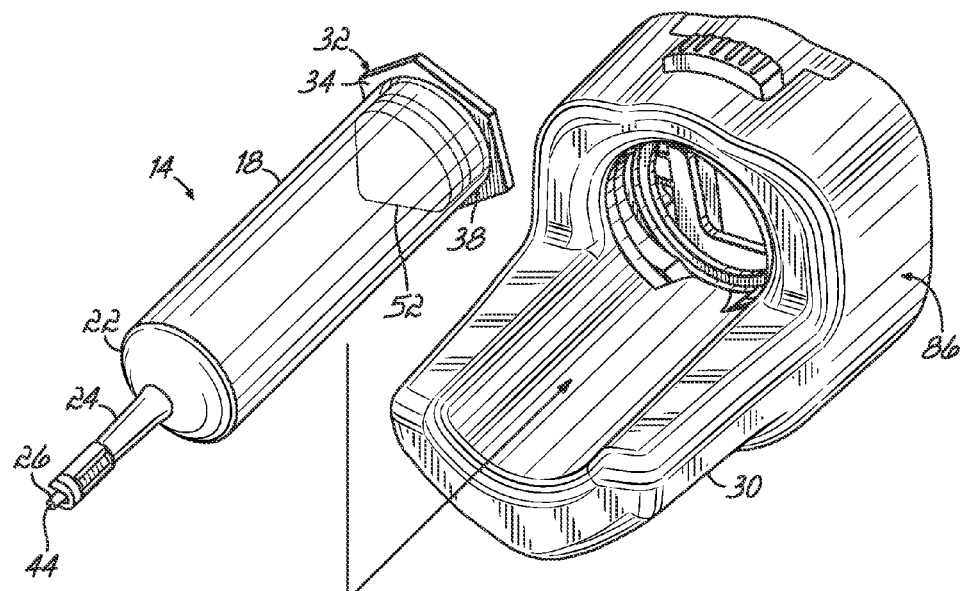
FIG. 2B is a perspective view of the syringe mount of FIG. 2A in an assembled condition.
Figure 2A:
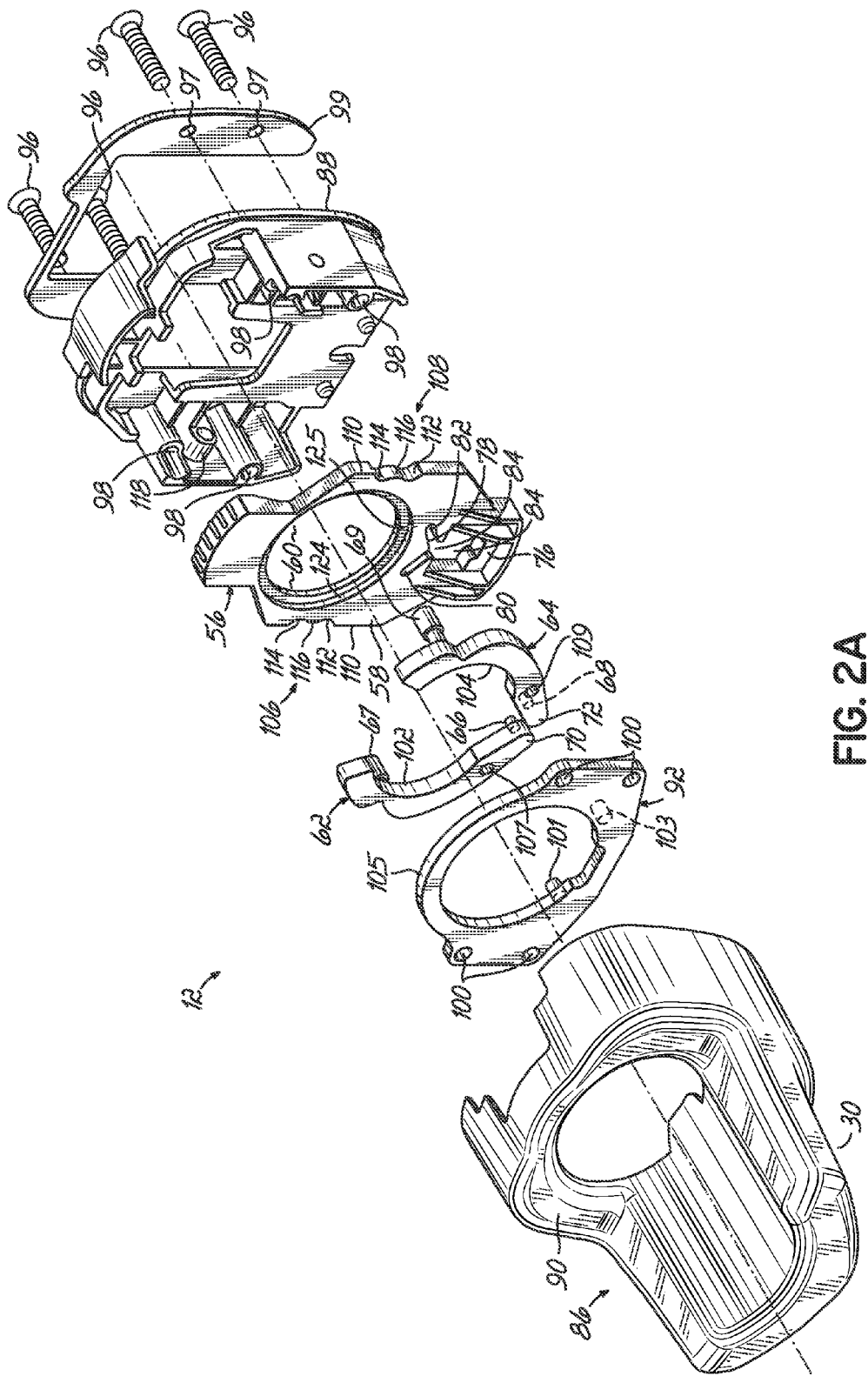
FIG. 2A is an exploded view of one exemplary embodiment of a syringe mount.
Figure 3B:
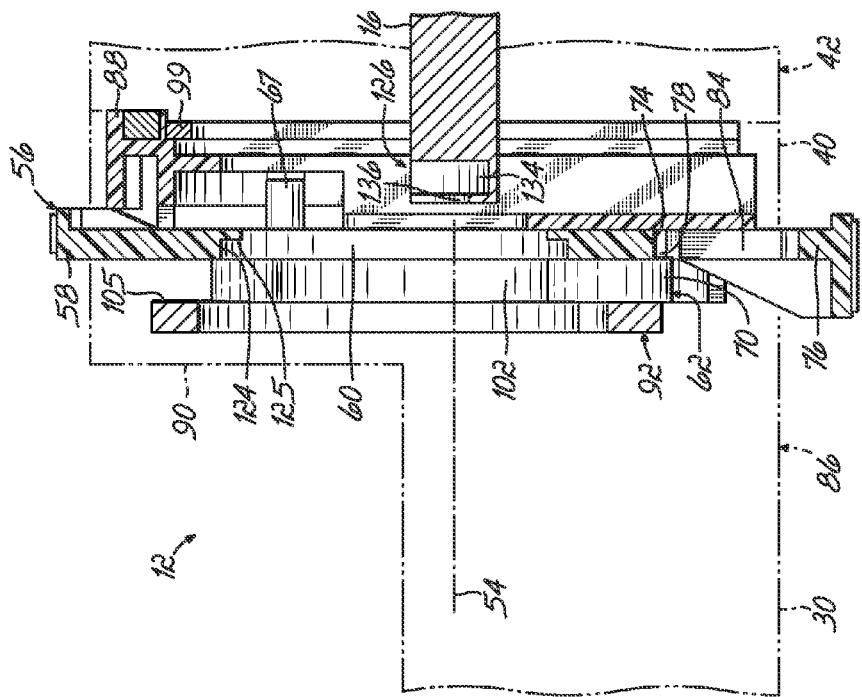
FIG. 3B is a cross-sectional view, taken along line 3B-3B of FIG. 3A.
Figure 3A:
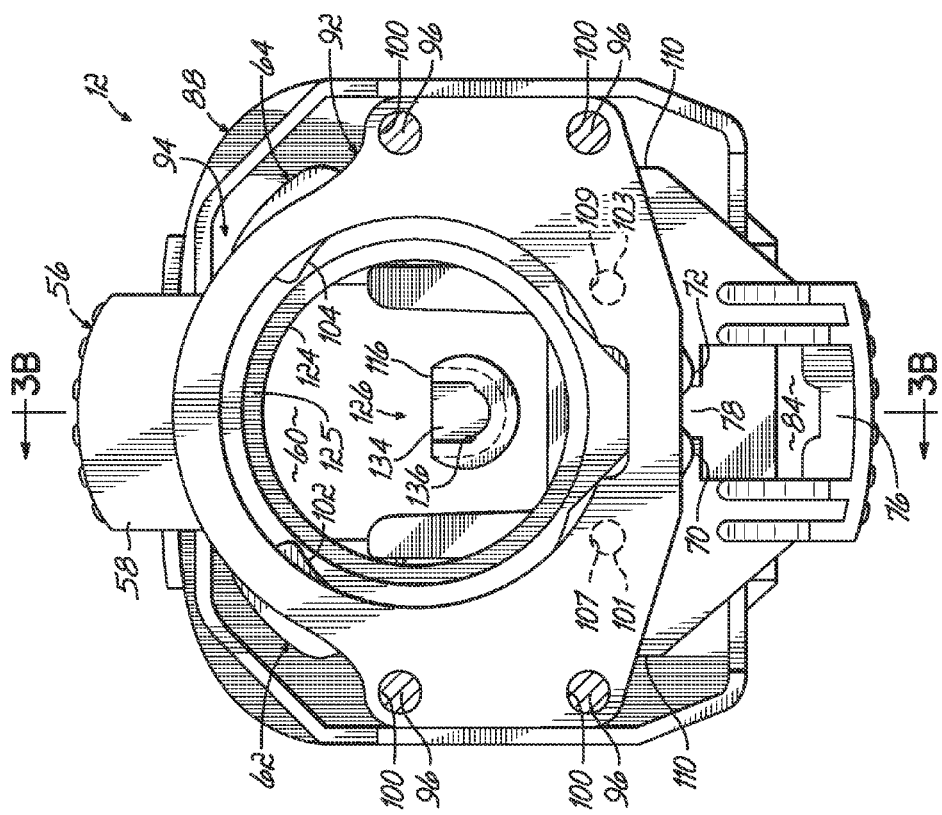
FIG. 3A is a cutaway view of the syringe mount of FIG. 2B, particularly showing an actuator of the syringe mount.

As can be seen from FIGS. 2A-5B, the actuator 56 and the first and second movable members 62, 64 of the syringe mount 12 are held within a face plate 86 of the housing 42 of the injector 10 (additional views of the face plate 86 may be seen in FIGS. 6-12). Referring particularly to FIG. 2A, the face plate 86 includes a proximal wall portion 88, a distal wall portion 90, a cradle 30 extending distally from the distal wall portion 90, and a coupling plate 92. The first and second movable members 62, 64 are located between the coupling plate 92 and the wall member 58 of the actuator 56, and all three components are then contained within an interior cavity 94 of the face plate 86, formed between the proximal wall portion 88 and distal wall portion 90. The actuator 56 and the first and second movable members 62, 64 are movable within the interior cavity 94. The coupling plate 92 is preferably substantially immobile relative to the proximal and distal wall portions 88, 90 of the face plate 86, as it is preferably fixed to at least one of the proximal and distal wall portions 88, 90. In the illustrated embodiment, this fixing occurs through the use of screws 96, which extend through orifices 97 in a rear plate 99, orifices 98 in the proximal wall portion 88, orifices 100 in the coupling plate 92, and are received in orifices (not shown) in the distal wall portion 90.

The coupling plate 92 includes first and second pivoting shafts 101, 103 projecting from a proximal surface 105 thereof. These first and second pivoting shafts 101, 103 are received in first and second shaft openings 107, 109 defined in the first and second movable members 62, 64, respectively. As such, the first and second movable members 62, 64 are able to exhibit a pivoting motion about the corresponding first and second pivot shafts 101, 103. Stated another way, the first and second movable members 62, 64 are coupled with corresponding the first and second pivoting shafts 101, 103 in a manner such that the movable members 62, 64 can pivot thereabout. The first and second pivoting shafts 101, 103 thus may be said to provide pivot points for the first and second movable members 62, 64.

To initiate loading of the syringe 14 into the syringe mount 12, the flange 34 at the rearward end 38 of the syringe 14 may be passed through an aperture in each of the distal wall portion 90 of the syringe mount 12 and the coupling plate 92 and may be received into the orifice 60 defined in the actuator 56. While the rearward end 38 of the syringe 14 is located in the orifice 60, the syringe 14 may be moved in a first direction substantially perpendicular to the longitudinal axis 54 of the drive ram 16 of the injector 10. Herein, this direction will be referred to as a "downward" direction (as the motion is down relative to the injector 10). However, it will be recognized by those skilled in the art that the motion does not have to be "downward," but that the components of the syringe mount 12 can be configured such that motion in other directions can effect appropriate engagement of the syringe 14 (including, but not limited to, "upward" movement, "side-to-side" movement, or any other appropriate, substantially perpendicular movement such that the longitudinal axis 36 of the syringe 14 is moved into a substantially coaxial relationship with the longitudinal axis 54 of the drive ram 16). This downward motion, in turn, responsively moves the actuator 56 in the downward direction. The motion of the actuator 56 in the downward direction causes each of the first and second pins 66, 68 to move to the corresponding first and second ends 80, 82 of the slot 74 defined in the base portion 76 of the wall member 58. This movement of the pins 66, 68 occurs because the first and second movable members 62, 64 cannot move in the downward direction due to the first and second pivoting shafts 101, 103 of the fixed coupling plate 92 being located within the first and second shaft openings 107, 109 of the first and second movable members 62, 64. Thus, as the actuator 56 moves in the downward direction, the first and second pins 66, 68 move within the slot 74 to the first and second terminal ends 80, 82 thereof. Because the first and second movable members 62, 64 cannot move downwardly, they instead pivot about the pivot points provided by the first and second pivoting shafts 101, 103. In other words, the first and second movable members 62, 64 rotate about the corresponding first and second pivoting shafts 101, 103 at the respective first and second shaft openings 107, 109. As such, the first and second movable members 62, 64 pivot to engage (e.g., substantially, circumferentially envelop) the rearward end 38 of the syringe 14 (see FIG. 5A). Since the flange 34 of the syringe 14 is located within the actuator 56 during this pivoting movement of the movable members 62, 64, the first and second movable members 62, 64 engage the body 18 of the syringe 14 (rather than the flange 34). In embodiments where the movable members 62, 64 are designed such that this engagement with the body 18 of the syringe 14 may be characterized as a substantial enveloping of the body 18, it may be said that this type of engagement allows for greater coverage of the syringe 14 than found in prior syringe mounts, and thus, potentially allows the syringe 14 to withstand greater injection pressures.

In the illustrated embodiment, the first and second movable members 62, 64 are opposite one another and are positioned about the longitudinal axis 54 of the drive ram 16. Further, the first and second movable members 62, 64 each have an arcuate face 102, 104. These arcuate faces 102, 104 are shown as being diametrically opposite one another and located exterior to the body 18 of the syringe 14. When the syringe 14 is properly engaged with the syringe mount 12 of the injector 10, the first and second movable members 62, 64 of the syringe mount 12 are in contact with the side surface of the exterior body 18 of the syringe 14 to hold the syringe 14 in place and in alignment with the drive ram 16 of the injector 10.

In some embodiments, the arcuate faces 102, 104 of the movable members 62, 64 may bear one or more types of engagement enhancing features (e.g., grooves, bumps, indentations, ridges, teeth, combinations thereof, and the like) to improve the ability of the movable members 62, 64 to grip and/or hold the syringe 14. In some embodiments, a grip enhancing coating (e.g., Santoprene® elastomer) may be applied to the arcuate faces 102, 104 of the movable members 62, 64 to facilitate gripping/holding of the syringe 14.

The pivotal movement of the first and second movable members 62, 64 alters the distance between the arcuate faces 102, 104 as they pivot toward and away from one another. In the illustrated embodiment, the first and second movable members 62, 64 are each movable. In some embodiments, it is possible to use a single movable member disposed in spaced relation to an immobile member (e.g., arcuate stop or abutment) toward which the single movable member may be moved.

In some embodiments, first and second movable members 62, 64 are not necessary for appropriate syringe engaging function. In such embodiments, a single gripping member may be used to engage the syringe 14, thereby operatively connecting the syringe 14 to the injector 10. In such embodiments, the single movable member should cover enough of the circumference of the syringe 14, when in contact with the body 18, to hold the syringe 14 against the injector 10. In such embodiments, each arm extending from a center point of the movable member may have a degree of elasticity such that the arms may splay outwardly and inwardly to allow for insertion and/or removal of the syringe 14.

The wall member 58 of the actuator 56 is shown as having a peripheral side surface 110 that includes a first undulating contour 106 and a second undulating contour 108. As shown, the second undulating contour 108 is positioned substantially opposite the first undulating contour 106. Each of these first and second undulating contours 106, 108 includes a first valley 112, a second valley 114, and a ridge 116 disposed therebetween. When positioned within the syringe mount 12 of the injector 10, these first and second undulating contours 106, 108 are confronted by first and second projections 118, 120 (see FIGS. 2A and 5A), which are adapted to ride along the surface of the first and second undulating contours 106, 108 as the actuator 56 is moved between the first and second positions. In the illustrated embodiment, the first and second projections 118, 120 are coupled to the proximal wall portion 88 of the face plate 86, and are spring-biased in a direction toward each of the first and second undulating contours 106, 108. The interaction of the first and second detents 118, 120 and first and second undulating contours 106, 108 assist in maintaining the actuator 56 in either the first or second position until a user desires to move the actuator 56 to either load or unload the syringe 14. In some embodiments, the first and second pins 66, 68 may include bias springs associated with each of the first and second movable members 62, 64. In such embodiments, one end of each of the bias springs may be in contact with its respectively associated movable member, and the opposite end of each bias spring may seat or bear against portions of the housing 42 (or face plate 86) of the injector 10. In some embodiments, at least a portion of these bias springs may be disposed about the pins 66, 68, which form the pivot axes of the first and second movable members 62, 64.

Figure 4A:
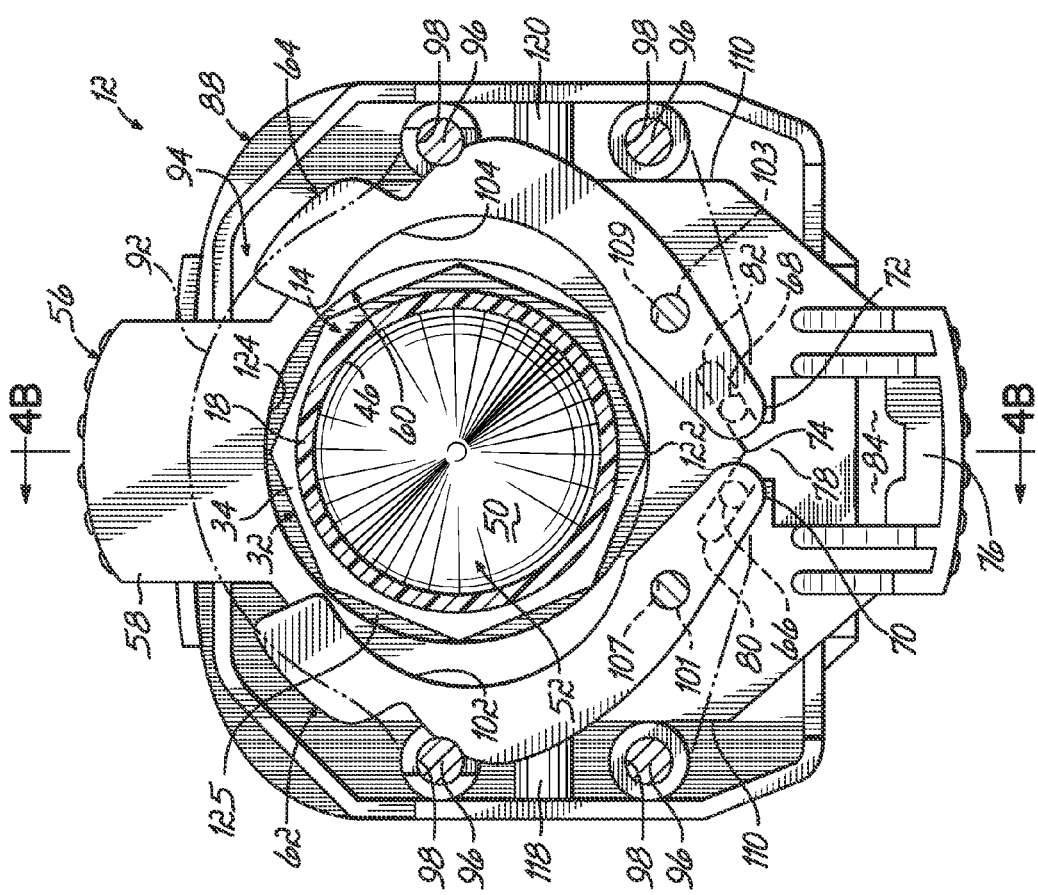
FIG. 4A is a cutaway view of syringe mount of FIG. 2B, particularly showing first and second movable members of the syringe mount in an open position.

To load a syringe 14 into the injector 10, the syringe 14 is positioned relative to the wall member 58 of the actuator 56 such that the flange 34 at the rearward end 38 of the syringe 14 is received within the orifice 60 of the wall member 58 such that at least one contact point 122 on the periphery of the flange 34 contacts or can be brought into contact with a peripheral surface 124 defining the orifice 60. More specifically, the flange 34, in certain embodiments, may be received by a recess 125 in the actuator 56. The actuator 56 is shown in FIG. 4A as being in the first position, such that the first and second movable members 62, 64 are in the open position. Also in this first position, the first and second projections 118, 120 are in contact with the first valleys 112 of the corresponding first and second undulating contours 106, 108. The force of the spring bias of the first and second projections 118, 120 at least assists in preventing the wall member 58 of the actuator 56 from moving unassisted to the second position. Further, the drive ram 16 of the injector 10 is preferably positioned such that a plunger coupling mechanism 126 is aligned with a coupling mechanism 128 extending from a rearward face of the syringe plunger 52 (see FIG. 4B).

A user then applies a force to the syringe 14 in a direction substantially perpendicular to, and towards, the longitudinal axis 54 of the drive ram 16. The flange 34 of the syringe 14, contacting the peripheral surface 124 of the wall member 58, is utilized to force the wall member 58 of the actuator 56 to responsively move in a direction substantially perpendicular to the longitudinal axis 54 of the drive ram 16. Enough force is applied to overcome the spring-bias of the first and second projections 118, 120, such that the actuator 56 moves from the first position to the second position. As this occurs, the first and second projections 118, 120 ride along the first and second undulating contours 106, 108 from the first valleys 112, along the ridges 116, and into the second valleys 114. The first and second projections 118, 120 may then be utilized to at least assist in maintaining the wall member 58 in the second position shown in FIG. 5A.

The movement of the wall member 58 from the first position to the second position cooperatively moves the slot 74 of the wall member 58 in a direction substantially perpendicular to the longitudinal axis 54 of the drive ram. And thus, the slot 74 moves relative to the first and second pins 66, 68, thereby causing the first and second pins 66, 68 to move relative to and within the slot 74. More specifically, in the illustrated embodiment, the first and second pins 66, 68 move within the V-shaped slot from a position proximal to the point of the "V," to positions proximal to the terminal ends of each leg of the "V" (from the position shown in FIG. 4A, to the position shown in FIG. 5A). This movement causes a responsive pivotal movement of the first and second movable members 62, 64 from the open position to the closed position such that the rearward end 38 of the syringe 14 is engaged by the first and second movable members 62, 64. In particular, as the actuator 56 moves in the downward direction, the first and second pins 66, 68 move within the slot 74 to the first and second terminal ends 80, 82 thereof. Because the first and second movable members 62, 64 cannot move downwardly, they instead pivot about the pivot points provided by the first and second pivoting shafts 101, 103. In other words, the first and second movable members 62, 64 rotate about the first and second pivoting shafts 101, 103 at the first and second shaft openings 107, 109, respectively.

As the wall member 58 is moved from the first position to the second position, and the syringe 14 moves with the wall member 58 from a position not engaged by the movable members 62, 64 to a position engaged by the movable members 62, 64, the coupling mechanism 128 at the rearward end 38 of the syringe plunger 52 moves from a position not engaged with the plunger coupling mechanism 126 of the drive ram 16 to a position engaged with the plunger coupling mechanism 126 of the drive ram 16. In the illustrated embodiment (see FIGS. 4B and 5B), when the flange 34 of the syringe 14 is aligned with the orifice 60 defined by the wall member 58, the syringe plunger 52 within the syringe 14 is preferably positioned such that the coupling mechanism 128 on the rearward face of the syringe plunger 52 is aligned with the plunger coupling mechanism 126 of the drive ram 16. The coupling mechanism 128 of the illustrated syringe plunger 52 is a projection 128 extending from the rearward face of the syringe plunger 52. This projection 128 may be characterized as exhibiting a "T" shape having a stem portion 130 (parallel to the longitudinal axis 36 of the syringe 14) topped by a cap portion 132 (transverse to the longitudinal axis of the syringe 14). As the wall member 58 is moved from the first position to the second position, the cap portion 132 of the coupling mechanism 128 may be received by the plunger coupling mechanism 126, which in the illustrated embodiment, is a slot 134 formed in the forward end of the drive ram 16.

A slot 134 is defined in the forward end of the drive ram 16 in a shape to receive the coupling mechanism 128 of the syringe 14, and particularly the cap portion 132 thereof. A cross-section of the plunger coupling element 126 is shown as exhibiting a J-shape (having a slot within a hook portion of the "J" configured to receive the cap portion 132), such that when the syringe plunger 52 is engaged with the drive ram 16, the distal end 136 of the "J" shape is positioned distally of a part of the cap portion 132 of the coupling mechanism 128. Thus, when the syringe 14 is initially inserted into the actuator 56 (in the first position), the cap portion 132 of the coupling mechanism 128 is "above" the plunger coupling element 126 of the drive ram 16. However, as the actuator 56 is moved to the second position, the cap portion 132 of the coupling mechanism 128 is moved to be positioned proximally of the distal end 136 of the plunger coupling mechanism 126 of the drive ram 16. Once engaged, an injection procedure may be run, such as by translating the drive ram 16 forward along its longitudinal axis 54 to dispense a fluid, such as contrast media, from the syringe 14. While the slot 134 and extension 128 of the illustrated embodiment have shapes referred to herein as "J" and "T," respectively, it will be recognized by those of skill in the art that any shape that facilitates coupling may be used. Additionally, while the illustrated embodiment depicts first a coupling mechanism 128 and plunger coupling mechanism 126 that result in a passive coupling, those of skill in the art will recognize that coupling mechanisms and plunger coupling mechanisms that result in an active coupling (one which involves some degree of positive gripping) may be used.

As described previously, the syringe mount 12 of the present invention allows for the syringe 14 to be removed from the face plate 86 and/or forward end 40 of the injector 10, when the drive ram 16 of the injector 10 is at any position. It does not require the drive ram 16 to be returned to a "home" position before detaching the syringe 14 from the injector 10. Thus, during an injection procedure, the translation of the drive ram 16 may be stopped while the drive ram 16 is in an extended position from the front face place 86 of the injector 10. A user can then grip the syringe 14 and move it in an upward direction, thereby overcoming the spring-biased force of the first and second projections 118, 120 to cause the actuator 56 to move from the second position to the first position. As this occurs, the first and second projections 118, 120 ride along the first and second undulating contours 106, 108 from the second valleys 114, over the ridges 116, and into the first valleys 112. Simultaneously, the first and second pins 66, 68 of the first and second movable members 62, 64 will move within the V-shaped slot of the wall member 58 from a position near the terminal ends 80, 82 of the arms of the V to a position near the point of the V. This causes the first and second movable members 62, 64 to pivot from the closed position to the open position by pivoting about the pivot points created by the interaction of the first and second pivoting shafts 101, 103 with the first and second shaft openings 107 109. Due to the positioning of the flange 34 at the rearward end 38 of the syringe 14 within the orifice 60 of the actuator 56, the actuator 56 allows for enough vertical syringe movement for the T-shaped coupling mechanism on the rearward face of the syringe 14 to clear the slot on the forward end of the drive ram 16, thereby allowing removal of the syringe 14 from the injector 10.

Additional advantages and modifications will readily appear to those skilled in the art. The invention in its broader aspects is therefore not limited to the specific details, representative apparatus and methods, and illustrative examples shown and described. Accordingly, departures may be made from such details without departing from the scope or spirit of Applicant's general inventive concept.

What is claimed is:

1. A method of using a syringe mount of a medical fluid injector, the medical fluid injector comprising a drive ram having a longitudinal axis, the method comprising:
   moving a syringe through an aperture of the syringe mount and into an interior cavity of the syringe mount to insert the syringe into a separate orifice defined in a first component of the syringe mount;
   moving the first component in a first direction substantially perpendicular to a longitudinal axis of the syringe to move the longitudinal axis of the syringe towards the longitudinal axis of the drive ram, wherein the syringe is located within the orifice during the moving of the first component; and
   the moving of the first component causing movement of a second component of the syringe mount toward the longitudinal axis of the syringe.

2. The method of claim 1, wherein the moving of the second component comprises moving opposing first and second portions of the second component toward the longitudinal axis of the syringe, wherein the longitudinal axis of the syringe is located between the first and second portions prior to and after the moving of the second component.

3. The method of claim 1, wherein the second component of the syringe mount contacts the syringe as a result of the moving of the second component.

4. The method of claim 1, wherein the aperture is defined in a third component of the syringe mount.

5. The method of claim 4, wherein the moving of the first component comprises moving the first component relative to the third component.

6. The method of claim 4, wherein the moving of the second component comprises moving the second component relative to the third component.

7. The method of claim 4, wherein the syringe is disposed within the aperture and orifice of the first and third components, respectively, during the moving of the first component.

8. The method of claim 1, further comprising a user of the syringe mount exerting a force on the syringe while the syringe is located within the orifice defined in the first component, wherein the force exerted by the user comprises a force vector oriented in the first direction, and wherein the force exerted by the user causes the moving of the first component.

9. The method of claim 1, wherein the moving of the first component changes the position of the orifice relative to the longitudinal axis of the drive ram.

10. The method of claim 1, wherein the moving of the first component changes a position of the longitudinal axis of the syringe relative to the longitudinal axis of the drive ram.

11. The method of claim 1, wherein the moving of the syringe is executed with the first component being in a first position, wherein the longitudinal axis of the syringe is spaced from the longitudinal axis of the drive ram with the first component being in the first position, wherein the moving of the first component moves the first component from the first position to a second position, and wherein the moving of the first component moves the longitudinal axis of the syringe into a substantially coaxial relationship with the longitudinal axis of the drive ram.

12. A method of using a syringe mount of a medical fluid injector, the medical fluid injector comprising a drive ram having a longitudinal axis, the method comprising:
  moving a syringe parallel to the longitudinal axis of the drive ram to insert the syringe into an orifice defined in a first component of the syringe mount;
  moving the first component in a first direction substantially perpendicular to a longitudinal axis of the syringe to change the position of the orifice of the first component relative to the longitudinal axis of the drive ram; and
  the moving of the first component causing movement of a second component of the syringe mount toward the longitudinal axis of the syringe.

13. The method of claim 12, wherein the moving of the second component comprises moving opposing first and second portions of the second component toward the longitudinal axis of the syringe, wherein the longitudinal axis of the syringe is located between the first and second portions prior to and after the moving of the second component.

14. The method of claim 12, wherein the second component of the syringe mount contacts the syringe as a result of the moving of the second component.

15. The method of claim 12, further comprising inserting the syringe into an orifice defined in a third component of the syringe mount.

16. The method of claim 15, wherein the moving of the first component comprises moving the first component relative to the third component.

17. The method of claim 15, wherein the moving of the second component comprises moving the second component relative to the third component.

18. The method of claim 15, wherein the syringe is disposed within the orifices of the first and third components during the moving of the first component.

19. The method of claim 12, further comprising a user of the syringe mount exerting a force on the syringe while the syringe is located within the orifice defined in the first component, wherein the force exerted by the user comprises a force vector oriented in the first direction, and wherein the force exerted by the user causes the moving of the first component.

20. The method of claim 12, wherein the moving of the first component changes a position of the longitudinal axis of the syringe relative to the longitudinal axis of the drive ram.

21. The method of claim 12, wherein the moving of the syringe is executed with the first component being in a first position, wherein the longitudinal axis of the syringe is spaced from the longitudinal axis of the drive ram with the first component being in the first position, wherein the moving of the first component moves the first component from the first position to a second position, and wherein the moving of the first component moves the longitudinal axis of the syringe into a substantially coaxial relationship with the longitudinal axis of the drive ram.

22. A method of using a syringe mount of a medical fluid injector, the medical fluid injector comprising a drive ram having a longitudinal axis, the method comprising:
  moving a syringe in an insertion direction to insert the syringe into an orifice defined in a first component of the syringe mount; and
  moving the first component in a first direction substantially perpendicular to a longitudinal axis of the syringe to change a position of the longitudinal axis of the syringe relative to the longitudinal axis of the drive ram, wherein the insertion and first directions are different, and wherein the moving of the first component is while the syringe is located within the orifice and causes movement of a second component of the syringe mount toward the longitudinal axis of the syringe.

23. The method of claim 22, wherein the moving of the second component comprises moving opposing first and second portions of the second component toward the longitudinal axis of the syringe, wherein the longitudinal axis of the syringe is located between the first and second portions prior to and after the moving of the second component.

24. The method of claim 22, wherein the second component of the syringe mount contacts the syringe as a result of the moving of the second component.

25. The method of claim 22, further comprising inserting the syringe into an orifice defined in a third component of the syringe mount.

26. The method of claim 25, wherein the moving of the first component comprises moving the first component relative to the third component.

27. The method of claim 25, wherein the moving of the second component comprises moving the second component relative to the third component.

28. The method of claim 25, wherein the syringe is disposed within the orifices of the first and third components during the moving of the first component.

29. The method of claim 22, further comprising a user of the syringe mount exerting a force on the syringe while the syringe is located within the orifice defined in the first component, wherein the force exerted by the user comprises a force vector oriented in the first direction, and wherein the force exerted by the user causes the moving of the first component.

30. The method of claim 22, wherein the moving of the syringe is executed with the first component being in a first position, wherein the longitudinal axis of the syringe is spaced from the longitudinal axis of the drive ram with the first component being in the first position, wherein the moving of the first component moves the first component from the first position to a second position, and wherein the moving of the first component moves the longitudinal axis of the syringe into a substantially coaxial relationship with the longitudinal axis of the drive ram.

31. A method of using a syringe mount of a medical fluid injector, the medical fluid injector comprising a drive ram having a longitudinal axis, the method comprising:
  inserting a syringe into an orifice defined in a first component of the syringe mount and while the first component is both in a first position and interconnected with the medical fluid injector, wherein a longitudinal axis of the syringe is spaced from the longitudinal axis of the drive ram with the first component being in the first position; and moving the first component from the first position to a second position while the syringe is located within the orifice, wherein the moving of the first component is in a first direction substantially perpendicular to the longitudinal axis of the syringe, causes movement of a second component of the syringe mount toward the longitudinal axis of the syringe, and moves the longitudinal axis of the syringe into a substantially coaxial relationship with the longitudinal axis of the drive ram.

32. The method of claim 31, wherein the moving of the second component comprises moving opposing first and second portions of the second component toward the longitudinal axis of the syringe, wherein the longitudinal axis of the syringe is located between the first and second portions prior to and after the moving of the second component.

33. The method of claim 31, wherein the second component of the syringe mount contacts the syringe as a result of the moving of the second component.

34. The method of claim 31, further comprising inserting the syringe into an orifice defined in a third component of the syringe mount.

35. The method of claim 34, wherein the moving of the first component comprises moving the first component relative to the third component.

36. The method of claim 34, wherein the moving of the second component comprises moving the second component relative to the third component.

37. The method of claim 34, wherein the syringe is disposed within the orifices of the first and third components during the moving of the first component.

38. The method of claim 31, further comprising a user of the syringe mount exerting a force on the syringe while the syringe is located within the orifice defined in the first component, wherein the force exerted by the user comprises a force vector oriented in the first direction, and wherein the force exerted by the user causes the moving of the first component.

* * * * *